(12) United States Patent
Laird et al.

(10) Patent No.: US 6,445,956 B1
(45) Date of Patent: Sep. 3, 2002

(54) IMPLANTABLE MEDICAL DEVICE

(75) Inventors: John D. Laird, Kittery Point, ME (US); Lawrence E. Stanton, Burlington; Richard L. Reveal, Andover, both of MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/419,943

(22) Filed: Oct. 18, 1999

(51) Int. Cl.[7] .................................................. A61N 1/02
(52) U.S. Cl. .............................. 607/61; 607/36; 607/37
(58) Field of Search .................................. 607/36–38, 1, 607/2, 32–33, 60, 61

(56) References Cited

U.S. PATENT DOCUMENTS

| | | | | |
|---|---|---|---|---|
| 3,866,616 A | * | 2/1975 | Purdy et al. | 607/36 |
| 3,987,799 A | * | 10/1976 | Purdy et al. | 607/36 |
| 4,143,661 A | | 3/1979 | LaForge et al. | |
| 5,109,843 A | | 5/1992 | Melvin et al. | |
| 5,350,413 A | * | 9/1994 | Miller | 607/61 |
| 5,411,537 A | * | 5/1995 | Munshi et al. | 607/33 |

OTHER PUBLICATIONS

Melvin, D.B., et al., "Electric Power Induction Through an Isolated Intestinal Pouch" (1991) *Trans. Am. Soc. Intern. Organs*, vol. XXXVII; M203–M204.

Masuzawa, T., et al., "Set–up, Improvement, and Evaluation of an Electrohydraulic Total Artificial Heart with a Separately Placed Energy Converter" (1996) *ASAIO Journal*, vol. 42; M328–M332.

Robert O. Rawson et al., Visceral Tissue Vascularization: An Adaptive response to High Pressure, 158 Science 1203.

Wayne F. Larrabee, Jr., MD et al., *Wound Tension and Blood Flow in Skin Flaps*, 112 (1984).

Charles R. Davies et al., Adaptation of Tissue to a Chronic Heat Load, ASAIO Journal M514 (1994).

* cited by examiner

*Primary Examiner*—George R. Evanisko
(74) *Attorney, Agent, or Firm*—Nutter, McClennen & Fish, LLP

(57) ABSTRACT

A medical device for implantation and a TET system which includes the device as a component are provided. The device is designed so that it does not substantially restrict blood flow in the tissue surrounding the implanted device, thereby minimizing the risk of ischemia and necrosis. This enables the device to be implanted near tissue layers that are otherwise susceptible to blood flow restrictions when a device of the same volume and height is implanted. Blood flow adequate to prevent ischemia and necrosis is maintained by minimizing extravascular tissue pressure caused by the implantation of the device.

8 Claims, 4 Drawing Sheets

IMPLANTABLE MEDICAL DEVICE

BACKGROUND OF THE INVENTION

1. Field of the Invention

The present invention relates generally to medical devices and, more particularly, to implantable medical devices.

2. Related Art

Many medical devices such as pacemakers, defibrillators, circulatory assist devices, cardiac assist and replacement devices, cochlea implants, neuromuscular simulators, biosensors, implantable drug delivery pumps and the like are now designed to be implanted in humans or animals. Because many of these devices require a source of power, inductively coupled transcutaneous energy transfer (TET) systems are coming into increasing use. A TET system may be employed to supplement, replace, or charge an implanted power source, such as a rechargeable battery. Unlike other types of power transfer systems, TET systems provide power to the implanted electrical and/or mechanical device, or recharge an internal power source, without use of a percutaneous lead. Thus, possibilities of infection are reduced and comfort and convenience are increased.

Generally, TET systems include a transcutaneous transformer having an external primary coil operationally aligned with an implanted secondary coil. An external power source is connected to a primary circuit that drives the primary coil to induce alternating current in the secondary coil. This alternating current is converted to direct current by a secondary circuit to provide power to the implanted device or power source. The non-implanted portions of conventional TET systems, including the primary coil and its drive circuitry, are attached externally to the patient, typically by a belt or other fastener or garment.

Implantable medical devices must be carefully designed with respect to both volume and shape in order to minimize the risk of ischemia (shortage of blood supply to tissue) which may eventually lead to necrosis (tissue death). This is particularly true for medical devices that are implanted in subcutaneous tissue. The secondary coil of a TET, for example, may be implanted between the dermis layer of the skin and the subcutaneous tissue. Accordingly, it has generally been recognized that the volume of subcutaneously implanted devices should be a minimum consistent with the functional integrity of the implanted device. In addition to designing implantable devices with a minimal volume, intuitive considerations have led designers to avoid sharp corners on the exterior surfaces of the device. However, it is not uncommon for implanted medical devices to cause eventually ischemia and necrosis of the surrounding tissue. This is especially true of devices that dissipate energy in the form of heat, such as the secondary coil of a TET system.

SUMMARY OF THE INVENTION

The invention provides an implantable medical device shaped such that, when implanted, it does not substantially restrict blood flow in the tissue surrounding the implanted device, thereby minimizing the risk of ischemia and necrosis. This enables the device to be implanted near tissue layers that are otherwise susceptible to blood flow restrictions when a device of the same volume is implanted. Blood flow adequate to prevent ischemia and necrosis is maintained by minimizing extravascular tissue pressure caused by the implantation of the device. The device may be implanted at locations that cause a layer of tissue to overlay at least one surface of the implanted device. The overlaying tissue layer may be any combination of cutaneous, muscle or fat tissue.

In one aspect of the invention, an implantable device designed to be implanted within a body is provided. The implantable device includes a body section having an exterior shaped to maintain, when the device is implanted under a layer of tissue, extravascular tissue pressure below intravascular blood pressure in the layer of tissue proximate to the implanted device.

In another aspect of the invention, an implantable device designed to be implanted within a body is provided. The implantable device includes a body section including a curved, tissue-overlaying surface having a radius of curvature of greater than approximately 1 cm.

In one aspect of the invention, a transcutaneous energy transfer system is provided. The system includes a primary coil positionable external of a body and a secondary coil housed in a device implantable under a layer of tissue. The primary coil is designed to induce an alternating current in the secondary coil. The device includes a body section having an exterior shaped to maintain, when the device is implanted under a layer of tissue, extravascular tissue pressure below intravascular blood pressure in the layer of tissue proximate to the implanted device.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of minimizing ischemia. Further features and advantages of the present invention as well as the structure and operation of various embodiments of the present invention are described in detail below with reference to the accompanying drawings.

BRIEF DESCRIPTION OF THE DRAWINGS

The invention will now be described by way of example, with reference to the accompanying drawings, in which.

DETAILED DESCRIPTION

Figure 1:
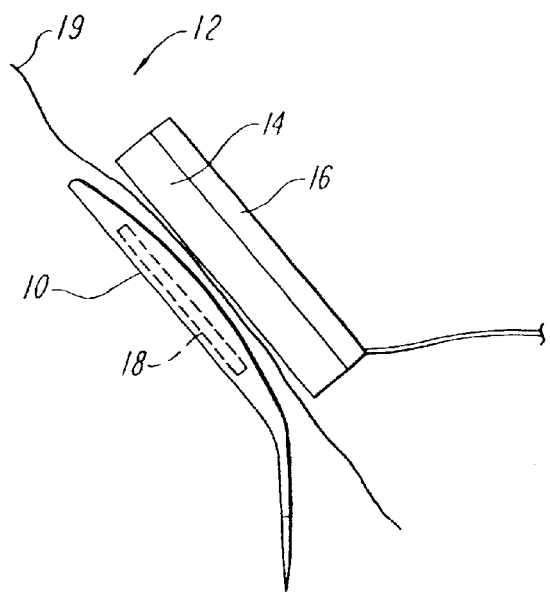
FIG. 1 is a diagrammatic representation of a TET system.
Figure 2:
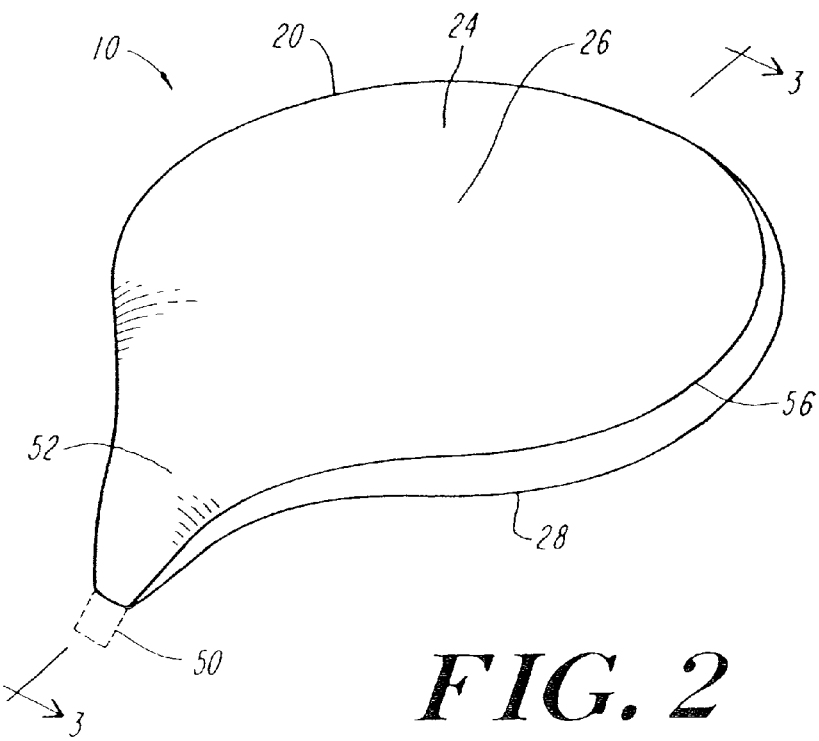
FIG. 2 is a perspective view of an implantable medical device according to one embodiment of the present invention.

An implantable medical device of the present invention is shaped such that, when implanted, it does not restrict substantially blood flow in the tissue surrounding the implanted device, thereby minimizing the risk of ischemia and necrosis. This enables the device to be implanted near tissue layers that are otherwise susceptible to blood flow restrictions when a device of the same volume and height is implanted. Blood flow adequate to prevent ischemia and necrosis is maintained by minimizing extravascular tissue pressure caused by the implantation of the device.

In one embodiment, an implantable medical device adapted for implantation beneath the dermis layer of skin tissue in a human or animal is illustrated in FIGS. 1–4. An implantable medical device 10 may be a component of an implanted medical system, such as a total artificial heart (TAH) system or a ventricular assist device (VAD) system. In the example shown in FIG. 1, the implantable device 10 is a component of a transcutaneous energy transfer (TET) system 12, which is used primarily to supply power the TAH, the VAD or any other implanted medical device requiring power.

The TET system 12 includes a transcutaneous transformer having an external primary coil 14 with corresponding circuitry 16, and an implanted secondary coil 18 (shown in phantom) housed within the implantable device 10 with corresponding circuitry (not shown). Circuitry 16 is powered by an external source, for example a battery, and is designed to drive the primary coil 14 to induce alternating current in the subcutaneous secondary coil 18. The alternating current is typically converted to a direct current which may be used to power the TAH or other implanted medical device.

The device 10 is typically implanted between the dermnis layer of the skin 19 and the subcutaneous tissue, as will be further described further below. The non-implanted portions of conventional TET systems are attached externally, typically by a belt or other fastener or garment, such that the primary coil 14 of the TET system 12 is operationally aligned with the implanted secondary coil 18.

Although the invention is shown and described with reference to a component of a TET system implanted under the dermis layer, it is to be appreciated that the present invention may be implemented in any implantable medical device in any location where it is desirable that the device have minimal adverse effect on blood flow in overlaying tissue. In particular, any type of tissue, such as muscle, fat, skin, and combinations thereof, may overlay the implanted device.

Some medical devices, such as the secondary coil of a TET system, dissipate heat. It has been found that tissue temperature in excess of approximately 42° C. may cause necrosis. Thus, in order to maintain tissue temperatures below this level, blood flow to the area surrounding the implanted device should not be reduced below certain levels so that the blood may conductively remove the heat from the surrounding area. In this regard, the implantable device of the invention may be particularly useful when implemented in medical devices that dissipate heat. Because the implantable device of the invention ensures adequate blood flow to surrounding tissue, necrosis due to high tissue temperatures may also be prevented.

Figure 3:
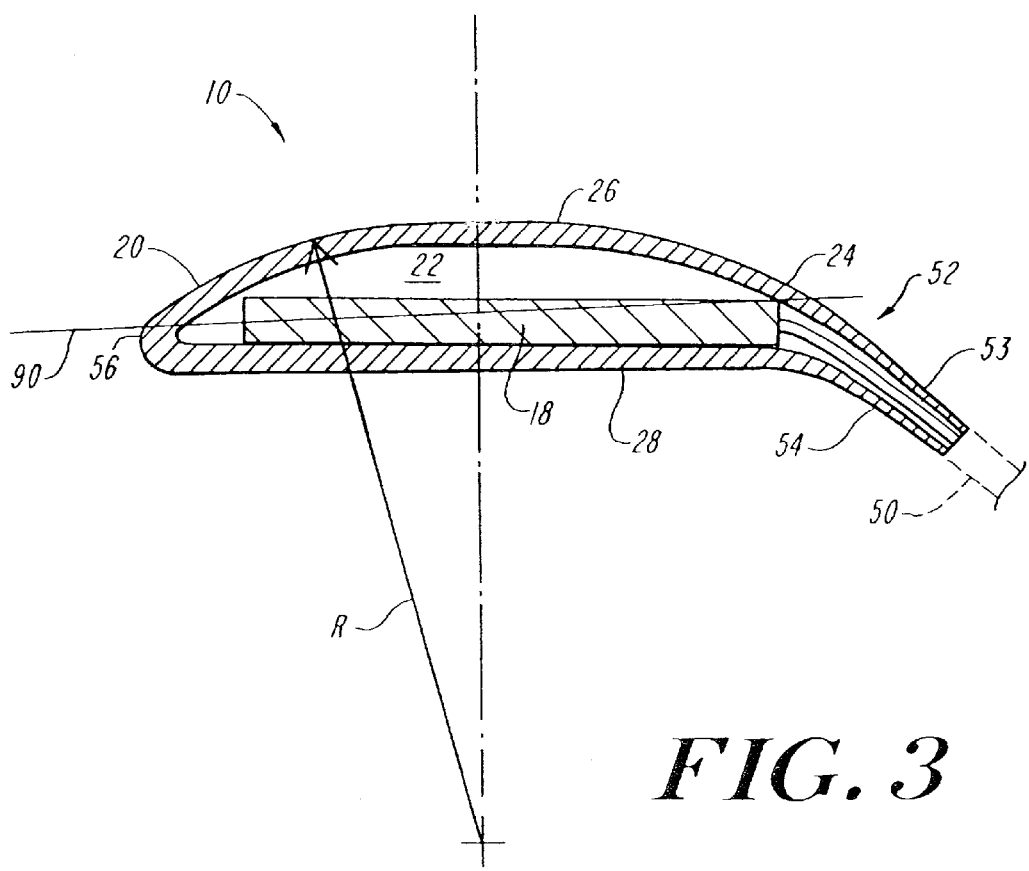
FIG. 3 is a cross-sectional view of the device taken along line 3—3 of FIG. 2.
Figure 4:
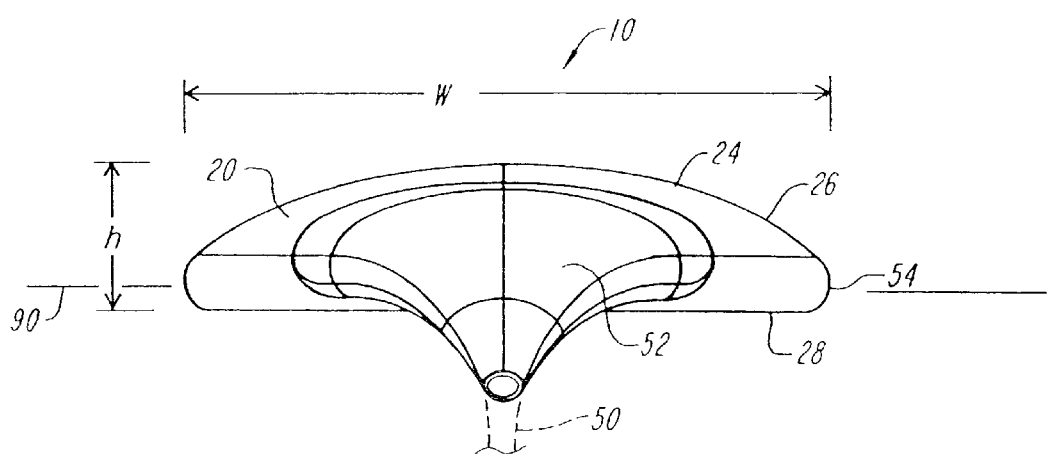
FIG. 4 is a side-view of the device of FIG. 2.

In the illustrative embodiment shown in FIGS. 1–4, the medical device 10 includes a disk-shaped body section 20 having an exterior 24, a height, h, and a width, w (FIG. 4). The exterior 24 of the body section 20 is shaped, as described further below, to maintain extravascular tissue pressure below intravascular blood pressure in tissue overlaying the implanted device. A cavity 22 (FIG. 3) within the body section 20 is adapted to house components of the medical device, in this embodiment, the TET secondary coil 18. The body section 20 may have a circular, elliptical, or other shape depending on use. In the illustrative embodiment, h is approximately 1.78 inches and w is approximately 7.87 cm, though any suitable dimensions may be used as required by the application.

The exterior 24 of the body section 20 includes a tissue-overlaying surface 26 and an opposing bottom surface 28. It is to be appreciated that the term "tissue-overlaying" is merely used to designate that portion of the exterior 24 adjacent the tissue layer that overlays the implanted device. Thus, because the device 10 in the example described herein is implemented to be implanted below the dermis layer, such as in the case of a TET secondary coil housing, the dermis layer is the overlaying tissue layer. The tissue-overlaying surface 26 has a shape that is adapted to minimize the effect of the implanted device on extravascular tissue pressure in the tissue surrounding the device and thereby prevent ischemia. In this regard, according to one embodiment of the invention, the tissue-overlaying surface 26 is curved and includes a radius of curvature "R", the magnitude of which is sufficient to maintain adequate blood flow in the dermis layer of the skin. The opposing surface 28 is adapted to conform to the area beneath the skin in which the device 10 is placed. Thus, the opposing surface 28 may be flat, concave, convex, or any other suitably-shaped surface.

As shown in FIGS. 3 and 4, the radius of curvature "R" extends over the entire tissue-overlaying surface 26. In other embodiments, rather, only a portion of the tissue-overlaying surface is curved as required to maintain extravascular tissue pressure below intravascular blood pressure in tissue overlaying the implanted device 10. In some embodiments, multiple radii of curvature "R" may be provided, such as may be the case with respect to a plane curve or a twisted curve. In certain cases when the tissue-overlaying surface 26 includes multiple radii of curvature, each of the radii of curvature may be joined to form a contiguous surface.

Generally, as described further below, the extravascular tissue pressure decreases with an increasing radius of curvature. Preferably, the tissue-overlaying surface 26 includes a minimum value of "R" to maintain extravascular tissue pressure below intravascular blood pressure which may depend upon several factors including the volume and shape of the device. Generally, when implanted beneath the dermis layer of the skin, the minimum value of "R" is at least greater than approximately 1.0 cm, in some cases greater than approximately 2.0 cm, and in other cases greater than approximately 4.0 cm. "R" generally does not have a maximum value above which the implanted device does not maintain extravascular tissue pressure below intravascular blood pressure, however, the maximum value of "R" may be constrained by the volume and shape of the implanted device and the location in which it is to be implanted. In the embodiment illustrated in FIGS. 2–4, the tissue-overlaying surface has a radius of curvature of between about 4.0 cm and about 11.7 cm.

Figure 5:
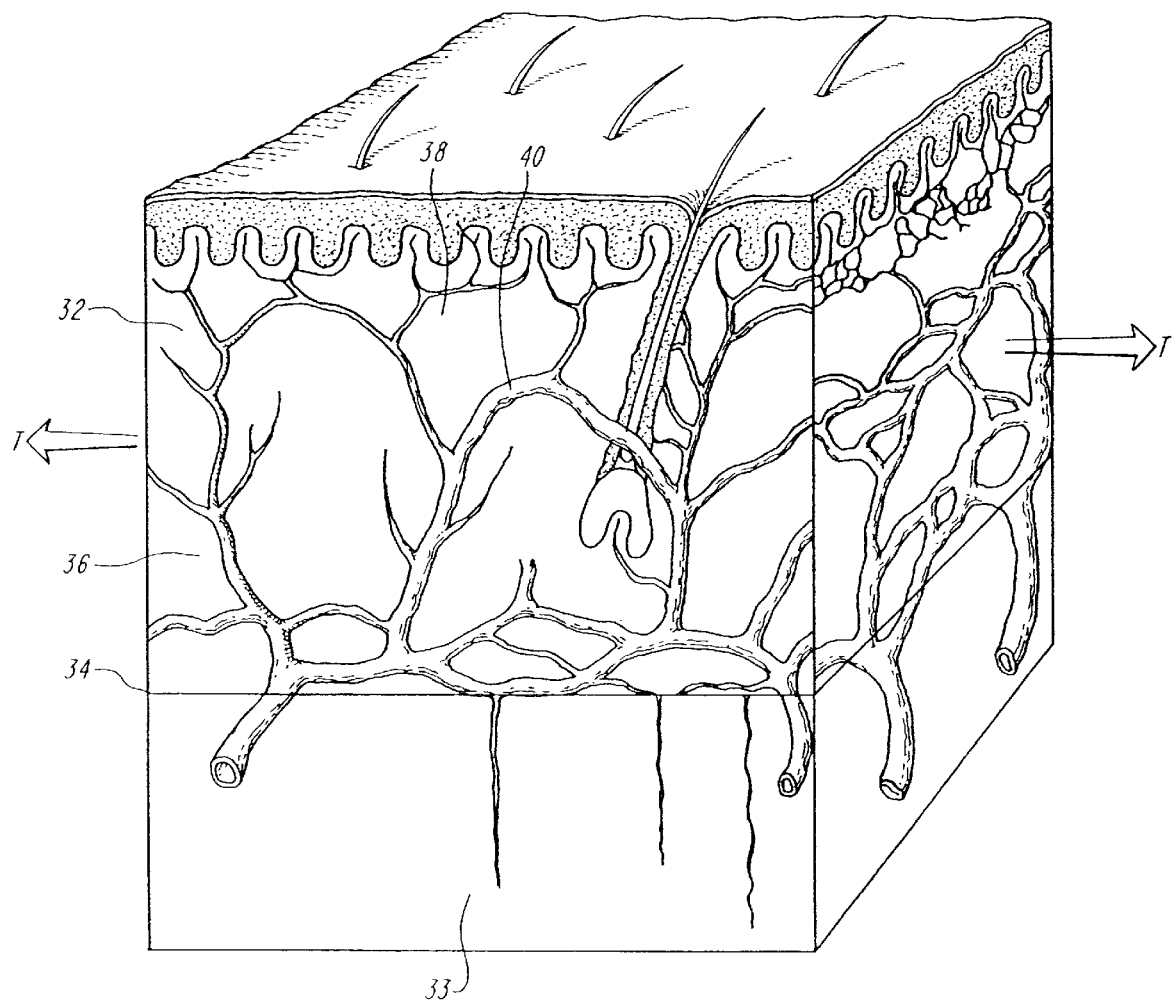
FIG. 5 is a diagrammatic illustration of the structure of the skin.

FIG. 5 is a diagrammatic representation of skin tissue 32 and subcutaneous tissue 33 depicted in Hammersen, Frithjof, "Histology—A color Atlas of Cytology, Histology and Microscopic Anatomy, Urban & Schwarzenberg", 2nd Edition, Baltimore-Munich, 1980. As noted, in certain applications the device 10 may be implanted at the interface 34 between dermis layer 36 of skin tissue 32 and subcutaneous tissue 33. Such a location may be selected when, for example, device 10 is required to be close to the surface of skin tissue 32, as is the case in the TET system described herein. Of course, device 10 may be implanted in other suitable locations, as described above, such as within or beneath subcutaneous tissue 32.

Depending on the volume and location of the device, implantation of the device will cause an increase in skin tension. For a device implanted subcutaneously at interface 34, the increase in skin tension is in the direction shown by arrows "T". This induced skin tension increases the effective extravascular tissue pressure in venous plexus 38 of skin tissue 32 that overlays the implanted device 10. Such an increase in tissue pressure will reduce blood circulation in the adjacent skin tissue when the extravascular tissue pressure exceeds the intravascular pressure of blood vessels 40 in the venus plexus 38. Thus, to maintain adequate blood flow, device 10 is shaped, as described above, such that the resulting extravascular tissue pressure is significantly less than the intravascular blood pressure. Generally, intravascular blood pressure is between approximately 15 mm Hg and 20 mm Hg. Therefore, it is preferable to maintain, when the device 10 is implanted, the extravascular tissue pressure at a value less than approximately 20 mm Hg, and, more preferably, at a value less than approximately 15 mm Hg. In some cases, depending on location of the body and the individual, the intravascular blood pressure may be outside of the range between 15 mm Hg and 20 mm Hg. Accordingly, in these cases, it is preferable to maintain extravascular tissue pressure below the intravascular blood pressure.

The relationship between the skin tension, the radius of curvature of the tissue-overlaying surface 26, and the extravascular tissue pressure may be approximated as set forth in Equation (1):

$$P_{tissue} = T/(f*R) \tag{1}$$

where, $P_{tissue}$=effective extravascular tissue pressure (N/m² or Pascals);

T=skin tension (N/m);

f=form factor (dimensionless); and

R=radius of curvature of the device (m).

The form factor (f) is a function of the shape of implantable device 10. This value is typically obtained through empirical testing, and ranges from 0.5 for a spherical shape to 1.0 for a cylindrical shape.

It is to be understood that Equation (1) is an approximation of the relation between the effective tissue-overlaying pressure and the radius of curvature. The relation is presented for illustrative purposes only. The actual relationship may be more complex.

Figure 6:
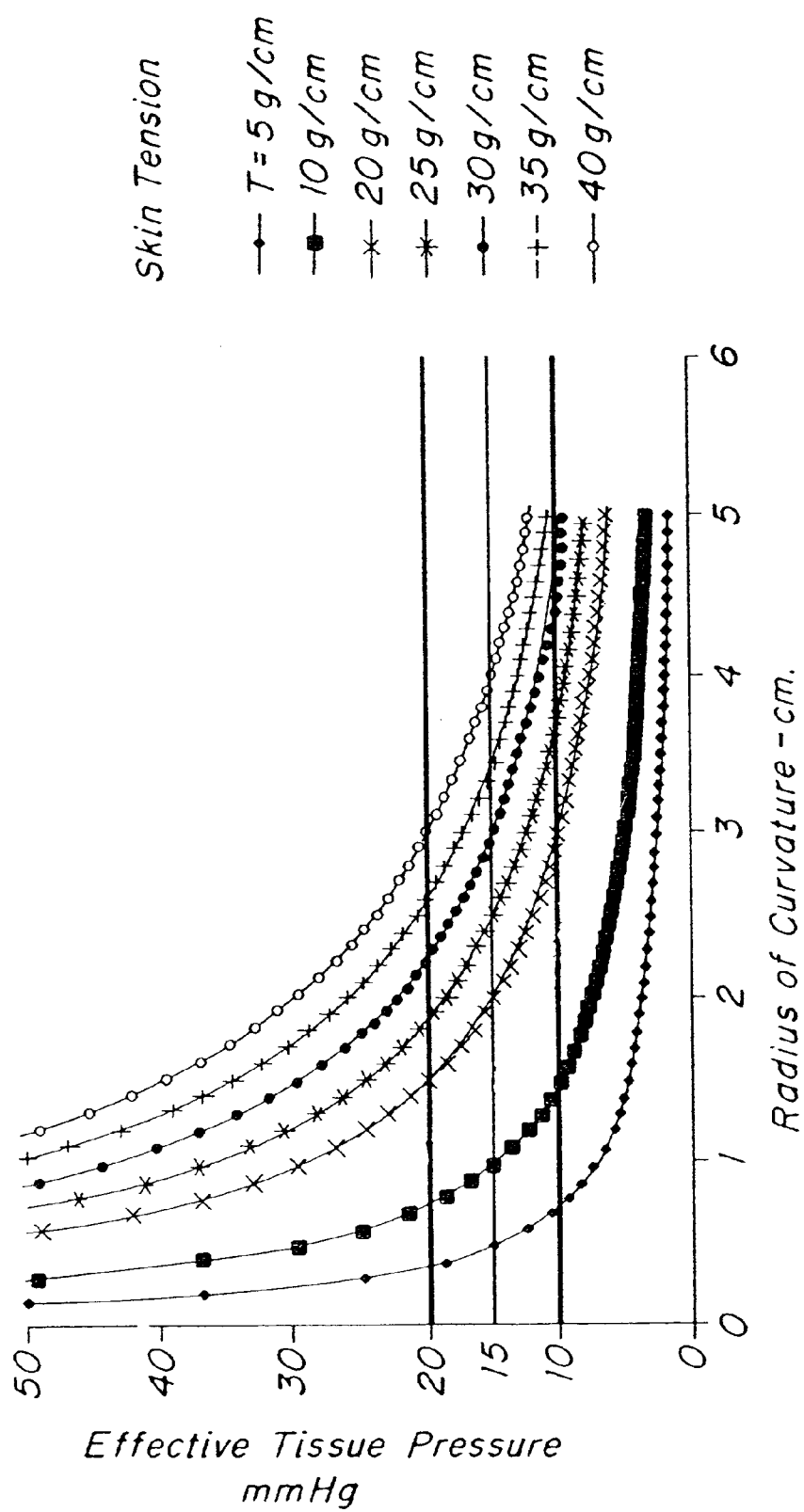
FIG. 6 is a graph showing a family of curves relating to the effect of the shape of the device on extravascular pressure.

FIG. 6 is a graph illustrating the relationship expressed in Equation (1) for device 10. The form factor, f, is approximated as 0.67 for the implantable device to generate the curves. A number of curves are illustrated, each representing the relationship between the effective tissue pressure and radius of curvature for a desired skin tension. From Equation (1) and the curves illustrated in FIG. 6, it is apparent that the extravascular tissue pressure for a given skin tension is inversely proportional to the radius of curvature "R" of skin-overlaying surface 26. Thus, it is desirable to increase the radius of curvature "R" to reduce extravascular tissue pressure, as described above.

The result of a study disclosed in W. F. Larrabee, and D. Sutton, Wound Tension and Blood Flow in Skin Flaps, Ann Otol Rhinol Laryngol 93:112–115 (1984) suggests that skin tension in excess of 80 g/cm for a substantially flat tissue layer results in necrosis. Thus, following the results of this study, avoidance of necrosis requires that the skin tension caused by an implantable device should be less than 80 g/cm, more preferably less than 40 g/cm, and more preferably still less than 20 g/cm. In the illustrative embodiment shown in FIG. 6, assuming an extravascular tissue pressure of 15 mm Hg, a radius of curvature of between about 2 cm and 4 cm results in a skin tension of between approximately 20 g/cm and 40 g/cm. According to the above-described study, such a skin tension will not cause necrosis. It is to be understood that the results of the study and the curves shown in FIG. 6 are merely presented for illustration and do not represent limitations of the invention.

As noted, exemplary implantable device 10 includes a secondary coil of a TET system. As such, device 10 provides power and/or data to an implanted medical device through a cable 50 (shown in phantom in FIGS. 2–4). To connect body section 20 to cable 50 while maintaining the induced extravascular tissue pressure within certain limits, device 10 is provided with a transition section 52. Transition section 52 is preferably tapered, providing a gradual transition from body section 20 to cable 50. In accordance with one embodiment of the present invention, transition section 52 is contiguous with tissue-overlaying surface 26 of body section 20. As shown best in FIGS. 3 and 4, transition section 52 is tapered in a plane 90 of body section 20 to reduce the size of the transition section 52. The reduced size decreases the likelihood that transition section 52 will cause ischemia. As shown best in FIG. 3, the transition section 52 also curves out of the plane 90. This provides an advantage in that portions with smaller dimensions of transition section 52 lie deeper within subcutaneous tissue 33 at a greater distance from skin tissue 32 than body section 20. Thus, in this aspect of the invention, the smaller dimensions of transition section 52 and, subsequently, cable 50, do not contribute significantly to the extravascular tissue pressure created in skin tissue 32 due to the implantation of device 10.

Referring to the figures, like body section 20, transition section 52 has a tissue-overlaying surface 53 and an opposing surface 54. The transition section 52 typically is designed with a minimum radius of curvature which may be substantially equivalent to the radius of curvature of the tissue-overlaying surface 26, or, in other embodiments, may have a different radius of curvature than the tissue-overlaying surface 26. In the illustrative embodiment, the transition section has a radius of curvature of between approximately 5.13 cm and 7.49 cm.

Edge 56 of the implantable device between the tissue-overlaying surface 26 and the opposing surface 28, may also be appropriately designed to reduce extravascular tissue pressure. Generally, however, the edge does not have an overlaying tissue layer and, thus, may not significantly effect extravascular tissue pressure. In preferred embodiments, the edge 56 has as large a radius of curvature as possible. In addition, the edge 56 may be positioned in an area containing muscle tissue or other subcutaneous tissue, which may be less affected by increased extravascular pressure.

While the best mode for carrying out the invention has been described in detail, those skilled in the art to which this invention relates will recognize various alternative embodiments including those mentioned above as defined by the following claims.

What is claimed is:

1. An implantable device designed to be implanted within a body, the implantable device comprising:

a body section having an exterior shaped to maintain, when the device is implanted under a layer of tissue, extravascular tissue pressure below intravascular blood pressure in the layer of tissue proximate to the implantable device and lower than 15 mm Hg, the body section including a curved surface adapted to be overlaid by tissue, the surface adapted to be overlaid by tissue being shaped by at least one radius of curvature wherein each of the at least one radius of curvature is greater than approximately 2 cm, the body section further including an opposing surface opposite the surface adapted to be overlaid by tissue, and wherein the body section defines a primary plane between the opposing surface and the surface adapted to be overlaid by tissue; and a transition section contiguous with the body section and connectable to a first end of a cable constructed to carry electrical signals, wherein the transition section curves away from the primary plane in a direction from the surface adapted to be overlaid by tissue toward the opposing surface.

2. The implantable device of claim 1, wherein the transition section tapers from a first size adjacent the body section to a second smaller size in a region adapted to be connectable to a cable.

3. The implantable device of claim 2, wherein when the body is adapted to be overlaid by dermal tissue, the transition section is configured to locate the region adapted to be connectable to a cable within subcutaneous tissue so that said region does not contribute to extravascular tissue pressure created in dernal tissue by implantation of the device.

4. The device of claim 1, wherein the device is a secondary coil of a transcutaneous transfer system and is adapted to receive transcutaneous energy transfer from a primary coil.

5. The implantable device of claim 1, wherein each of the at least one radius of curvature is. greater than approximately 4 cm.

6. The implantable device of claim 1, wherein the transition section has a different radius of curvature than each radius curvature of the body section.

7. The implantable device of claim 1, wherein the device is a transcutaneous energy transfer system component.

8. The implantable device of claim 1, further comprising a secondary coil housed within the body section.

* * * * *